(12) United States Patent
Postrel

(10) Patent No.: US 12,194,020 B2
(45) Date of Patent: Jan. 14, 2025

(54) REVERSING BALDNESS THROUGH CANNABINOID RECEPTOR ACTIVATION

(71) Applicant: Richard Postrel, Miami Beach, FL (US)

(72) Inventor: Richard Postrel, Miami Beach, FL (US)

( * ) Notice: Subject to any disclaimer, the term of this patent is extended or adjusted under 35 U.S.C. 154(b) by 172 days.

(21) Appl. No.: 17/722,325

(22) Filed: Apr. 16, 2022

(65) Prior Publication Data

US 2022/0249434 A1    Aug. 11, 2022

Related U.S. Application Data

(62) Division of application No. 15/954,582, filed on Apr. 16, 2018, now Pat. No. 11,331,300.

(60) Provisional application No. 62/609,384, filed on Dec. 22, 2017.

(51) Int. Cl.

| | |
|---|---|
| *A61K 31/353* | (2006.01) |
| *A61K 8/34* | (2006.01) |
| *A61K 8/44* | (2006.01) |
| *A61K 8/49* | (2006.01) |
| *A61K 8/63* | (2006.01) |
| *A61K 31/015* | (2006.01) |
| *A61K 31/05* | (2006.01) |
| *A61K 31/11* | (2006.01) |
| *A61K 31/198* | (2006.01) |
| *A61K 31/343* | (2006.01) |
| *A61K 31/568* | (2006.01) |
| *A61P 17/14* | (2006.01) |
| *A61Q 7/00* | (2006.01) |

(52) U.S. Cl.
CPC ............ *A61K 31/353* (2013.01); *A61K 8/347* (2013.01); *A61K 8/44* (2013.01); *A61K 8/498* (2013.01); *A61K 8/63* (2013.01); *A61K 31/015* (2013.01); *A61K 31/05* (2013.01); *A61K 31/11* (2013.01); *A61K 31/198* (2013.01); *A61K 31/343* (2013.01); *A61K 31/568* (2013.01); *A61P 17/14* (2018.01); *A61Q 7/00* (2013.01)

(58) Field of Classification Search
CPC .................................................... A61K 31/353
See application file for complete search history.

(56) References Cited

U.S. PATENT DOCUMENTS

| | | | | |
|---|---|---|---|---|
| 5,824,686 A | * | 10/1998 | Gormley | A61K 31/58 |
| | | | | 514/284 |
| 2006/0025448 A1 | * | 2/2006 | Lohray | A61K 31/415 |
| | | | | 514/406 |

* cited by examiner

*Primary Examiner* — Rei Tsang Shiao

(57) ABSTRACT

This invention reverses male pattern baldness by shocking dormant hair follicles out of their androgen induced hibernation phase back to the active hair-growing anagenic phase. The invention integrates two functions: 1) It blocks synthesis of compounds holding the follicles in the telogenic/hibernating phase and 2) It stimulates synthesis of compounds animating the hair-growing/anagenic phase in the follicular activity cycle. One preferred embodiment comprises an enzyme inhibitor blocking the conversion of testosterone to dihydrotestosterone (DHT), a flavonoid simultaneously increasing synthesis of prostaglandins alternative to prostaglandin $D_2$, and a selected cannabinoid compound stimulating restore the hair follicle to its normal growth cycle. This novel trimodal therapy restores the hair follicles to their normal cycling processes and maintains these restorative properties so long as this rebalance in maintained.

27 Claims, No Drawings
Specification includes a Sequence Listing.

REVERSING BALDNESS THROUGH CANNABINOID RECEPTOR ACTIVATION

Male pattern baldness, also known as androgenetic alopecia, is the common type of hair loss that develops in most men. Hair loss becomes noticeable generally between 25 and 50 years of age. The pace of hair loss differs greatly with progression to complete baldness in some scalp areas occurring over a range of about 5 to about 35 years from the start of hair loss.

This invention reverses the male pattern baldness process by shocking dormant hair follicles out of their androgen induced hibernation phase to restore the normal cycling pattern and thereby re-initiate the active hair-growing anagenic phase. The invention integrates two major functions: 1) It removes arresting influences that induce and maintain the telogenic or resting phase of the follicular cycle, and 2) It stimulates synthesis of compounds to refocus activity back to the hair-growing/anagenic phase of the cycle. One preferred embodiment comprises an enzyme inhibitor blocking the conversion of testosterone to dihydrotestosterone (DHT), a flavonoid simultaneously increasing synthesis of prostaglandins alternative to prostaglandin $D_2$, and a selected cannabinoid compound stimulating restore the hair follicle to its normal growth cycle. This novel trimodal therapy restores the hair follicles to their normal cycling processes and maintains these restorative properties so long as this rebalance in maintained.

Hair grows out of hair follicles (HF)s, tiny factories in the epithelium just under the skin surface. A follicle grows a single hair for about 30-40 months on average, with a range of about 24 to about 70 months still considered in the normal range. The follicle then terminates growth of that hair strand letting it naturally fall out as the follicle begins growing a new strand. This cycle of hair growth, shedding and new growth essentially determines the maximum length of a person's hair. In the balding process regional HFs of the scalp gradually decrease their size; the smaller follicle produces thinner hair strands; the diminished follicles shorten the time length for each strand to grow; maximum length decreases—eventually to a point where the stub of hair fails to breach the skin's outer surface.

The normal hair growth cycle comprises three phases: anagen, catagen, and telogen. The first growth phase, anagen, or hair growth phase, involves hair strand production over a period between two to six years. Then the anagen phase progresses to the catagen phase, a seven to fifteen day transition phase where strand growth ceases and the hair is released. This is followed by the telogen phase, a one to two month restoration/resting phase, before the anagen phase recommences. As the androgenic alopecia progresses the anagen growth phase diminishes in length as the telogen resting phase gains prominence.

Androgenetic alopecia has an androgenic etiology relating to dihydrotestosterone (DHT). DHT is the most abundant androgen in the skin and is made from testosterone by the 5-α reductase enzyme. The androgenic effect on hair is extremely site specific: hair on the chest, the pubic area, and lower face, e.g., beard area, is positively supported by the presence of androgens to grow thick, pigmented hair. Just a little higher on the body, HFs located on the scalp of the head respond to DHT (and similar androgens) by shrinking and making only nonpigmented vellus hairs.

According to the website: https://www.wikihow.com/Treat-Male-Pattern-Hair-Loss.
  a) Male pattern baldness is caused by genetic predisposition and the main androgen believed to be associated with baldness is dihydrotestosterone (DHT).
  b) Increased level of DHT in HFs is believed to shorten the hair's growth cycle and delay growth of new hair.
  c) Over time, the HFs stop growing new hair; however, the follicles remain alive, suggesting that they may still be able to grow new hair.

Baldness, particularly male pattern baldness, obviously has an underlying trait associated with male development. The androgenic hormone system comprises a class of steroid hormones whose increased concentration in males interacts with one or more of the androgenic receptors predominant in males. The androgens are steroid hormones primarily produced in and then secreted by the male testes. A secondary source of many androgens is the adrenal gland. Androgens are critical steroid hormones that regulate male sexual development and differentiation, including the formation of the reproductive system and maintenance of its function. Androgens are also involved in muscle development and psychosexual behavior. The major male androgen is testosterone. Testosterone derivatives, dihydrotestosterone (aka 5α-dihydrotestosterone) (DHT) and androstenedione are instrumental in male development. E.g., in utero, DHT directs differentiation of penis, scrotum and prostate. In later life, DHT contributes to balding, prostate growth, and sebaceous gland activity. DHT has a greater affinity for androgen receptors than testosterone. DHT is synthesized from testosterone by the enzyme 5α-reductase. DHT acts as the primary androgen in the genitals, prostate gland, seminal vesicles, skin, and HFs. 5α-Reductase inhibitors including, but not limited to: finasteride and dutasteride, inhibit 5α-reductase type 2 by direct binding and at maximum may decrease circulating DHT levels by 65 to 98%.

The present invention provides therapeutic products that arrest or reverse male pattern baldness, that restore hair growth to alopecic areas and/or that rebalance the growth and resting phases of hair follicle cycling. Product formats are not restricted and may be selected from any application methods acceptable to the user. For example, the therapeutic product may appear in a delivery format including, but not limited to: a liquid, a topical gel, mist, cream, low viscosity liquid, ointment, spray, dermal patch, shampoo, conditioner, etc. Following initial follicularly targeted microinjection, additional therapeutic treatments may be delivered by one or more topical treatments such as the creams or shampoo format. The additional therapeutic(s) follow the awakened ascending hair tracks to supplement and maintain directed stimulation. Supplements can be provided according to a preselected schedule and or in coordination with regular activity, such as a daily shower, a gym work out, a spa visit, etc., interspersed by one or more days, weeks, fortnights, etc. Microinjection is possible as discussed between the professional and the recipient. An initial flurry of treatments, e.g., weekly, may be tapered to bi-weekly, monthly, quarterly, etc., as decided by those involved.

The "arrest" process may commence at the earliest suspicion or detection of initiation of the male pattern baldness process, may commence based on family history, may commence based on racially or ethnically associated norms, may commence based on societal average, may commence based on suggestion, of friend family, co-worker etc., may commence upon completing a program, moving, starting new employment, etc., or may commence simply when the recipient desires or requests such action.

An especially robust delivery format comprises a wearable device situated upon the scalp. The device may include one or more features for analyzing scalp condition(s) and/or delivering stimulation to the underlying scalp. The analysis may, for example, determine the hair follicle density, the hair follicle activity state, the diameter and/or location of one or more hair shafts, nutritional indicators, etc. Stimulation may be mechanical, for example, a comforting or calming massage, and may be as intensive as featuring microinjectors to deliver therapeutic product to specific areas determined in advance or appropriately determined by the immediate analysis.

Two pharmaceuticals are FDA approved for androgenetic alopecia indications, minoxidil [hypertensive treatment] and finasteride [5-α reductase type 2 inhibitor]. Another compound, dutasteride, with stronger inhibitory efficacy than finasteride has undergone preliminary trials, but development has terminated in the US. Finasteride is a 5 α-reductase inhibitor available by prescription only. DHT is a derivative or enzymatic progeny of testosterone that appears to increase catagenic phase time at the expense of the anagenic. The 5-α-reductase converts testosterone to DHT which has stronger activity against hair growth than parent hormone molecule. DHT acts to shrink HFs, and when DHT is adequately suppressed, HFs should continue to thrive. DHT effect may be blocked or circumvented by depleting $PGD_2$.

Finasteride slows hair loss as long as you take it. However, as soon as you discontinue therapy, hair loss typically returns within a year. Side effects associated with finasteride include chills; cold sweats; confusion; dizziness; hives; swelling in the legs, arms and face; tingling; erectile dysfunction; decreased libido; and ejaculatory dysfunction; and weight gain.

Latanoprost, a prostaglandin analogue compound, approved for other indications, has been demonstrated to enhance eyelashes and in a 2011 study appeared to improve follicular activities. A Northwestern University sponsored trial (financed by Allergan) that was scheduled for completion in March 2017 included the following comment on ClinicalTrials.gov:

In addition to our observations with topical bimatoprost on fingernail growth, Wand and colleagues applied bimatoprost to the base of the fingernails demonstrating a 16.9% increase in fingernail growth from baseline, and a 10.4% increase from baseline on untreated nail beds. Other than these two reports, there are no studies addressing this topic to our knowledge based on a Medline search for off-label use of this drug. Other relevant studies have addressed increased hair and eyelash growth with the prostaglandin agents. Researching the biochemistry of the relationship of prostaglandins to hair and nail growth, the final common pathway appears to be with protein kinase C and the production of tropocollagens.

This trial of which the outcome is not known here supports continued research and conclusions presented in support of credibility of the present invention.

Minoxidil is an example of an accidental drug. During trials and use for controlling blood pressure, hair growth was a noted side effect. This apparently results from increasing the anagenic phase at the expense of the telegenic phase by activating PGHS 1 (prostaglandin endoperoxide synthase-1) in your system, helping to promote hair growth. However, side effects include skin irritation, itching, contact dermatitis, hives, swelling and sensitivity. Minoxidil is available as a topical foam or solution for rubbing or massaging into the skin of the scalp.

Male hormones, especially DHT and analogues, are involved in causing these alopecic changes. The level of the classic male hormone, testosterone, is indistinguishable between men with or without apparent baldness. In alopecia, cells in the skin of the scalp convert testosterone into DHT. These regional HFs become more sensitive to DHT, which then causes the HFs to shrink into the resting phase.

Saw palmetto is an effective anti-androgen. It acts in a similar way that Propecia does. Firstly, it lowers levels of DHT in the body by Blocking 5 α-reductase. Secondly, Saw palmetto blocks receptor sites on cell membranes required for cells to absorb DHT. Saw palmetto has been noted for its anti-oxidative and anti-inflammatory effects when supported with selenium and/or lycopene, especially plant derived lycopene, a non-flavonoid plant pigment.

Several flavonoid pigments including isoflavones can contribute to hair restoration or regrowth, e.g., by decreasing the length of the telegenic phase. Isoflavones are members of the larger family of compounds, known as flavonoids, which also includes flavones, flavanones, and flavans. These compounds are characterized by their phenyl side-chain, with a variable number of hydroxyl or other groups. Flavonoids with known hormonal influence include, but are not limited to: Genistein, Biochanin A, Luteolin, Daidzein, Naringenin, 7-Hydroxyflavone, 6-Hydroxyflavanone, Resveratrol, 6-Bromo-2-naphthol, Chrysin, Apigenin, 6-Hydroxyflavone, Morin, Fisetin, Quercetin, 7,8-Dihydroxyflavone, 4'-Hydroxyflavanone, 7-Hydroxyflavanone, Apigenin, Fisetin, Naringenin, Chrysin, Luteolin, Morin, etc. The specific mechanisms of action have not been proven for most of these compounds. Many combine an anti-androgenic and/or anti-estrogenic effect with anti-oxidant activity. Several have involvement in the arachidonic cascade. Such compounds may be used as supportive compounds for hair growth formulations of the instant invention.

Several thousand flavonoid compounds have been identified. Many are suggested at various websites for incorporation into food supplements. Such popular compounds include, but are not limited to: 3,3',4',5,7-pentahydroxyflavone, 2-(4-hydroxy-3-propoxy-phenyl)-chroman-3,5,7-triol, 2-(3-hydroxy-4-propoxy-phenyl)-chroman-3,5,7-triol; 2-(3-ethoxy-4-hydroxy-phenyl)-chroman-3,5,7-triol, 2-(4-ethoxy-3-hydroxy-phenyl)-chroman-3,5,7-triol, 2-(3,4-dihydroxy-phenyl)-3-propoxy-chroman-5,7-diol, methyl 4-((2R,3R)-3-hydroxy-5,7-dimethoxychroman-2-yl)-2-methoxybenzoate, methyl 5-((2R,3R)-3-hydroxy-5,7-dimethoxychroman-2-yl)-2-methoxybenzoate, (4-((2R,3R)-3-hydroxy-5,7-dimethoxychroman-2-yl)-2-methoxyphenyl)(4-methylpiperazin-1-yl)methanone, ethyl 2-(4-((2R,3R)-3-hydroxy-5,7-dimethoxychroman-2-yl)-2-methoxyphenoxy)acetate, ethyl 2-(5-((2R,3R)-3-hydroxy-5,7-dimethoxychroman-2-yl)-2-methoxyphenoxy)acetate, 2-(4-((2R,3R)-3-hydroxy-5,7-dimethoxychroman-2-yl)-2-methoxyphenoxy)acetic acid, ethyl 2-(2-hydroxy-4-((2R,3R)-3,5,7-trihydroxychroman-2-yl)phenoxy)acetate, ethyl 2-(2-hydroxy-5-((2R,3R)-3,5,7-trihydroxychroman-2-yl)phenoxy)acetate, (2R,3R)-2-(3,4-dihydroxyphenyl)-3-methoxychroman-5,7-diol, ((2R,3R)-2-(3,4-dihydroxyphenyl)-3-ethoxychroman-5,7-diol, (2R,3R)-2-(3,4-dihydroxyphenyl)-5,7-dihydroxychroman-3-yl acetate, 1-(((2R,3R)-2-(3,4-dihydroxyphenyl)-5,7-dihydroxychroman-3-yl)oxy)ethyl isobutyrate, W2R,3R)-2-(3,4-dihydroxyphenyl)-5,7-dihydroxychroman-3-yl)oxy)methyl diisopropylcarbamate, tert-butyl(W2R,3R)-2-(3,4-dihydroxyphenyl)-5,7-dihydroxychroman-3-yl)oxy)methyl)carbonate, 4-((2R,3R)-3,5,7-trihydroxychroman-2-yl)-1,2-phenylene dioctanoate, (2R,3R)-2-(3,4-dihydroxyphenyl)-5,7-dihydroxychroman-3-yl octanoate, (2R,3R)-2-(3,4-diacetoxyphenyl)chroman-3,5,7-triyl triacetate, 4-((2R,3R)-

3,5,7-trihydroxychroman-2-yl)-1,2-phenylene diacetate, 4-((2R,3R)-3,5,7-trihydroxychroman-2-yl)-1,2-phenylene diacetate, (2R,3R)-2-(3,4-dihydroxyphenyl)-3-methylchroman-3,5,7-triol, etc. One example of a patent extensively featuring flavonoids is U.S. Pat. No. 9,187,744, the contents of which are incorporated in their entirety by reference.

The *cannabis* plant itself contains flavonoids including, but not limited to: apigenin, luteolin, quercetin, kaemferol orientin, vitaxin, luteolin-7-O-glucoside, apigenin-7-O-glucoside cannflavins A and B, camphene, α-terpineol, α-eudesmol, α-selinene, fenchone, terpinolene, etc. Several, including luteolin, have been shown to inhibit $PGD_2$ or enhance an alternate pathway, e.g., PGE production, to divert $PGD_2$ fuel to alternate outcomes. Including such compounds in the product reduces or eliminates the telogenic enhancement effect seen in the presence of excess $PGD_2$.

For example, luteolin is marketed on the web as a supplement for multiple benefits, including as an antioxidant, mast cell activation inhibitor (possibly by blocking $PGD_2$ effect), free radical scavenger, histamine release blocker, GM-CSF release inhibitor, inhibitor of niacin flush. Luteolin and other flavonoids are available in small quantities in foods such as: celery, green pepper, thyme, perilla, chamomile tea, carrots, olive oil, peppermint, rosemary, navel oranges, and oregano. In general, $PGD_2$ inhibitors were formulated for use in treatment of allergic rhinitis, asthma, and other inflammatory disorders. In the past five years Luteolin and other $PGD_2$ inhibitors have been proposed as "cures for baldness". Yet to date none have been successful. Luteolin has been proposed for use in a homemade 5% topical solution ostensibly for anti-$PGD_2$. Simply stopping the $PGD_2$ effect apparently is not sufficient to return the follicular phasing to the anagenic dominant phase. However, the presence of $PGD_2$ also prevents removal of 5α-reductase inhibition from returning the cycle to anagenic dominance. Thus a preferred embodiment of the present invention features a nitric oxide activation and elimination or reduction of DHT and $PGD_2$ effects. Resveratrol, a natural phytocompound, selectively inhibits COX1 and blocks $PGD_2$ effects that support the telogenic phase over anagenic. Thus resveratrol with one or more nitric acid inducing compounds is part of one preferred embodiment.

In a typical presentation, hair begins to recede at the temples and on the crown of the head. A thinning hair region destined to become the bald patch gradually develops in the top-middle of the scalp. The receding regions from the temples and the bald patch spreading from the crown gradually expand to join together, often leaving an island patch at the front. This island patch, over time, thins as well.

Alopecia treatment requires prolonged compliance and patience. The gradual emphasis shift towards anagenic phase at the expense of telegenic phase does not present earth shattering results. Several months treatment is typical before noticeable effect. Compliance lapse, even for a short period, may require a new restart in the phase shifting processes. In the non-treatment interval, the follicles in the anagenic phase rapidly progress to catagenic phase and all the progress (the hair) becomes detached and falls out. Many months treatment benefit may be lost in just a few weeks.

With this background the present invention provides at least one alternative hair maintenance/hair growth paradigm. The effect(s) of cannabinoids (compounds that bind to and affect activity of at least one endocannabinoid receptor) demonstrate complexity in this area of biology. Given that DHT is instrumental in development of androgenic alopecia and that endocannabinoids and many phyto cannabinoids have been shown to interfere with DHT interacting with its receptor, one would expect that cannabinoids, by blocking the DHT effect, would prevent, stop, or at least slow hairloss. But a paper published in 2007, "Inhibition of human HF growth by endo- and exocannabinoids" showed the opposite.

The authors report:

$\Delta^9$-tetrahydrocannabinol (THC), the psychoactive component of marijuana, mimics the effects of numerous endogenous substances (collectively referred to as endocannabinoids) by binding to cannabinoid (CB) receptors. Centrally, these endogenous molecules are involved in regulating, e.g., behavior and learning, while their peripheral effects include the modulation of immune and cardiovascular functions and the control of growth normal and transformed cells as well as cell death and survival. CB receptors reportedly are also found on human epidermal keratinocytes in vitro, with conflicting data as to which types (CB1, CB2) are actually expressed. Although activation of CB receptors may suppress growth, murine skin tumors and human melanomas and, furthermore, cannabinoids were suggested to modify in vitro proliferation and differentiation of transformed keratinocytes, it is unclear whether CB receptors are functionally important in normal human skin physiology.

The organ culture of human scalp hair follicles (HF) in the growth stage of the hair cycle (anagen VI), which continue to grow rapidly after microdissection and produce hair shafts in vitro at almost the in vivo-speed seen on the human scalp, is ideally suited to follow-up the above reports of growth-modulatory effects of CB receptor ligands in the human system. Employing this assay, we had already shown, e.g., that vanilloid receptor-1 (TRPV1) agonists (such as capsaicin) operate as potent inhibitors of human hair growth. Arguing, furthermore, that the HF is exquisitely sensitive to the effects of psychoemotional stress; that THC is prominently incorporated into human hair shafts; and that several psychotropic hormones have recently been recognized to modulate human hair growth, we now have asked whether the endocannabinoid system is also involved in the control of human hair growth.

Since the cycling HF represents a prototypic, constantly remodeled epithelial-mesenchymal interaction system that switches between states of rapid epithelial proliferation (anagen), apoptosis-driven organ involution (catagen), and relative quiescence (telogen), the organ culture of human HF, which continues to undergo the anagen-catagen transformation in vitro, offers a highly instructive, easily accessible model for probing the effects of test agents on complex human tissue interaction systems. Therefore, as an integral part of the ongoing exploration of the intriguing "nonclassical" neuro-endocrine role of the skin both under physiological and pathological conditions, the human HF organ culture promised to offer an ideal, physiologically and clinically relevant general model system for dissecting the as-yet-unclear functions of cannabinoids in the control of human cell growth and death in situ.

The authors provide evidence that: 1) N-arachidonoylethanolamide (anandamide, AEA) significantly (P<0.05) and dose-dependently inhibited hair shaft elongation and hair matrix keratinocyte proliferation. 2) $CB_1$ binding activity is found in the HF epithelium, concentrated in the outer root sheath keratinocytes (but not so much in the fibroblasts of the HF dermal papilla. 3) transcription of the $CB_1$ gene but not the $CB_2$ gene was observed by RT-PCR in human scalp HFs. and 4) AEA stimulates apoptosis of cultured human HF. When anagen and catagen phase results were compared, $CB_1$ but not $CB_2$ transcription and expression are upregulated in catagen phase. Taken together these data suggest cannabinolic activity is important in phase timing and maintenance, $CB_1$, and not $CB_2$ is the more relevant cannabinoid receptor of this pair. Previous data had suggested another cannabinoid receptor, TRPV1, when activated inhibits hair shaft elongation (growth) and induces apoptosis-driven catagen regression. Thus both TRPV1 and $CB_1$ are candidates for action in hair loss and hairline regression.

This paper also reports endocannabinoid synthesis of $CB_1$ of dissected HF approximated that of cardiac tissue, but that $CB_2$ synthesis was about half that of cardiac. With respect to comparative effects of endogenous cannabinoid and those of THC this paper teaches: "THC significantly inhibited hair shaft elongation in a dose-dependent fashion, suppressed proliferation of HF keratinocytes, and induced both hair matrix keratinocyte apoptosis and premature catagen development. These data, therefore, suggest that exocannabinoids can mimic the hair growth-inhibitory effects of endocannabinoids." These and other data led authors of this paper to conclude: "AEA (which may even be produced within human HF), and the—notoriously abused—exocannabinoid, THC, both inhibit human hair shaft elongation and induce apoptosis-driven HF involution (catagen) in vitro."

The cannabinoid blockade of the DHT driven androgenic alopecic effects would suggest that applying exocannabinolic compounds or increasing endocannabinoid synthesis. However, in view of this 2007 paper and other similar teachings, the DHT inferred understanding that exposure of a scalp HF to an endo- or exo-cannabinoid would result in noticeable increase in hair growth, including at least either number of active follicles or hair length is shown to be faulty.

AEA and other cannabinoids exert their impacts in various manners. One important manner, especially with respect to HF is production of nitric oxide (NO). Both AEA and 2AG have been shown to be effective NO inducers. NO is probably most noted for its involvement in male erection and as a target of erectile dysfunction drugs. NO is implicated as the main vasoactive nonadrenergic, noncholinergic neurotransmitter and chemical mediator of penile erection. In this capacity, NO activates soluble guanylyl cyclase thereby initiating a chain of events that causes the smooth muscle of corpora cavernosa to relax and absorb blood. Released by nerve and endothelial cells in the corpora cavernosa of the penis, NO activates soluble guanylyl cyclase, which increases 3',5'-cyclic guanosine monophosphate (cGMP) levels.

In addition to modulating NO levels, AEA also mediates the inhibition of LPS-induced AA and prostaglandin apparently through a $CB_2$ activation pathway. In contrast, 2AG itself may serve as an AA precursor for metabolism by COX2 to $PGE_2$ countering $PGD_2$ synthesis.

Activation of $CB_1$ and/or $CB_2$ as well as TRPV1 results in increased NO. Increasing NO by these methods overcomes or bypasses the inhibitory effects of DHT and shifts HFs away from the catagenic phase and more towards the anagenic.

AEA is also stored esterified to phosphatidylethanolamines and is released by the action of phospholipase D. AEA or another cannabinoid of choice may be delivered as the drug itself or as a pro-drug, e.g., AEA may be effectively delivered as, for example, a pro-drug C20:4-N-arachidonoyl-phosphatidylethanolamine for conversion to AEA by the a/J3-hydrolase 4 pathway; a prodrug C20:4-N-arachidonoyl-phosphatidylethanolamine for conversion to AEA by the soluble phospholipase A2 pathway; a pro-drug C20:4-N-Arachidonoyl-phosphatidylethanolamine for conversion to AEA by the protein tyrosine phosphatase 22/SH2-containing inositol-5-phosphatase pathway; a pro-drug C20:4-N-arachidonoyl-phosphatidylethanolamine for conversion to AEA by the N-arachidonoyl-phosphatidylethanolamine-phospholipase D pathway; AEA epoxide, already a $CB_2$ agonist, may be activated by cytochrome p450; etc.

Compounds such as secretoneurin that are known to stimulate NO production and release but have not yet been characterized to identify all receptors to which it binds are considered as cannabinolic compounds when their application has results in line with those of known cannabinoids. The term "cannabinoid active" is thus used to include compounds with cannabinolic activity regardless of whether they have been identified as binding a cannabinoid receptor.

Inhibiting MAGL and/or FAAH, preferably by topical application, but alternatively by systemic application can prolong the effects of the hair stimulating cannabinoids.

Directing more AA which is often considered the rate limiting compound to destinies other than $PGD_2$ is one means of minimizing the $PGD_2$ anti-hair growth effect and will rebalance the HF metabolism back towards the anagenic phase. In this vein, a membrane-bound glutathione (GSH)-dependent $PGE_2$ synthase (mPGES), continuation enzyme of the cyclooxygenase 2 (COX2)-mediated $PGE_2$ biosynthetic pathway is one available tool. mPGES activity can be increased markedly at least in macrophages in response to various proinflammatory stimuli. In these circumstances, mPGES was functionally coupled with the induced COX2 in a marked preference to the constitutively expressed COX1, especially when AA was limited. Thus mild stress, such as a cannabinolic exposure may help tilt the COX pathways away from $PGD_2$ production. Coupling this with an inhibitor more specific for COX2 will produce stronger beneficial anagenic effect. At least with AEA there is evidence that the $PGE_2$ directed COX2 synthetic pathway is preferred over the COX1 pathway capable of making $PGD_2$. MIngYu, et al in "Synthesis of Prostaglandin E2 Ethanolamide from Anandamide by Cyclooxygenase-2" report that AEA did not serve as a substrate for COX1, but also that it did not compete with available AA in the COX1 pathway either. Excess or AEA undergoing removal advantageously does not risk feeding the $PGD_2$ induced hair growth inhibition. $PGD_2$ binds the GPR44 receptor. Interfering with this interaction, e.g., by reducing or blocking ligand or receptor or inhibiting downstream effects of the receptor bonding may be used as an adjunct or alternative to cannabinoid induced NO. Resveratrol has been shown to significantly suppress $PGD_2$ at low concentrations readily obtainable through oral dosing. In general, use of the terms COX2 inhibitor and COX1 inhibitor are meant to indicate that the inhibitor inhibits the numbered COX to a greater degree than the other COX. For example, valeryl salicylate would be considered a COX1 inhibitor because of its selective inhibition of the 1 isoform over that of the 2 isoform. Similar COX1 inhibitors include, but are not limited to: Cox-1 Inhibitor II, FR122047 hydrate, resveratrol, SC 560, etc. (Although resveratrol has capacity to inhibit COX2 also, resveratrol has greater inhibitory potency against COX1.) Meloxicam sodium salt would be a COX2 inhibitor. While ibuprofen, ketoprofen and sulfidics would be considered COX inhibitors, COX1/2 inhibitors or COX1 and COX2 inhibitors.

Two kinetically distinct prostaglandin biosynthetic responses, the immediate and delayed phases, imply involvement of different sets of the biosynthetic enzymes whose expression and activation are tightly regulated. In immediate PG biosynthesis, which occurs within several minutes after stimulation with agonists that increase cytoplasmic Ca' levels, cytosolic phospholipase A2 (cPLA2) is required for supplying membrane sourced AA to COX1. In the delayed and prolonged PG biosynthesis, which proceeds for a long time period after a stimulus, COX2, is an absolute requirement irrespective of the constitutive presence of COX1. cPLA2 and several inducible secretory phospholipase A2 isozymes cooperatively contribute to supply the AA to COX2. This preference of COX2 over COX1 may rest in the ability of COX2 to metabolize lower levels of AA to $PGH_2$ than the higher [AA] required for COX1-directed catalysis. Bimaprost (discussed above as an eyelash thickener) appears to work through this effect. There is evidence that at least some stress inducers not only divert AA to $PGE_2$ production, but also induce another parallel AA consuming pathway to produce prostacyclin ($PGI_2$).

In the last decade or so we have come to recognize that prostaglandin D2 ($PGD_2$) plays a primary role in hair loss. Scalp mast cells produce this prostaglandin. Two to three fold increases in scalp $PGD_2$ are reported in bald individuals. Like the endogenous endocannabinoids, $PGD_2$ synthesis includes arachidonic acid (AA) as a raw material in its synthetic pathway.

Arachidonic acid is acted on by a cyclooxygenase (COX1 or COX2) to form prostaglandin $G_2$ ($PGG_2$) which is rapidly COX converted to $PGH_2$. $PGH_2$ is a source of thromboxanes (e.g., $TXA_2$) (thromboxin synthase), $PGD_2$, $PGE_2$, $PGF_2$ and $PGI_2$ (prostacyclin synthase).

Two enzymatic steps are performed on the COX to convert AA to $PGH_2$. A cyclooxygenase portion catalyzes the conversion of AA to $PGG_2$ followed by peroxidase activity that reduces $PGG_2$ to $PGH_2$. COX1 and COX2 are two known isoforms capable of converting AA to PGH2 through a similar catalytic site and mechanism. A third Cox isoform, COX3, is encoded in the COX1 gene but with retention of intron 1 in the mRNA. The physiological function of this third isoform or possible other COX isoforms is unknown.

COX1 is constitutively expressed in most tissues and may regulate various homeostatic functions there. COX2 is inducible in many tissues and when induced regulates PG production during several acute responses such as inflammation. In general, non-steroidal anti-inflammatory drugs (NSAIDS) such as aspirin inhibit both COX1 and COX2. But inhibitors more selective for either COX1 or COX2 are available and under development.

After $PGH_2$ is synthesized the wide variety of PGs and related compounds including, but not limited to: thromboxanes, $PGD_2$, $PGE_2$, $PGF_2$, $PGI_2$, etc., can be produced in accord with the specific PG synthase enzymes present. For example, PGF-synthase enzyme has been cloned and is a member of the aldo-keto reductase family of enzymes that includes 20α-hydroxysteroid dehydrogenase.

COX2-dependent biological responses has received much attention in the past few years, because numerous pharmacological, biological and genetic studies have suggested that this inducible COX isozyme is involved in various human diseases, including inflammation and cancer and in a transformational patent case involving the University of Rochester. Generally, the main PG species produced during the delayed or induced response is $PGE_2$. Since COX2 inhibitors would reduce $PGE_2$ more profoundly than other PGs (e.g., $PGD_2$), COX2 inhibition is not a preferred adjunct to the present invention unless this increased $PGD_2$ synthesis is overcome or avoided.

PGES activity can be found in both cytosolic and membrane-associated fractions of most cells and tissues. This enzyme uses the anti-oxidant compound glutathione (GSH) as a cofactor for its catalytic effect. The first isolated and characterized PGES however showed preferential functional coupling with COX1.

A human microsomal GST-like 1 (MGST-L1) has now been identified and characterized as a member of the MAPEG (membrane-associated proteins involved in eicosanoid and GSH metabolism) superfamily. MGST-L1 exhibits significant PGES activity and is inducible using IL-1 in some cells. MGST-L1 appears identical to a membrane-associated PGES (mPGES), which has now been detected in lipopolysaccharide (LPS)-stimulated macrophages. MGST-L1/mPGES expression is strongly induced in vitro and in vivo. This mPGES/MGST-L1 is preferentially linked with COX2 pathways, promoting delayed and induced immediate $PGE_2$ biosynthesis rather than the inhibitory $PGD_2$. Furthermore, sustained expression of both COX2 and mPGES/MGST-L1 leads to aberrant cell growth. Our results indicate the presence of two segregated PGE2-biosynthetic routes, the cPLA2-COX1-cPGES/p23 and cPLA2-COX2-mPGES/MGST-L1 pathways, in the same cell.

The two main cannabinoids produced in mammalian, including human, body tissues are anandamide aka N-arachidonoylethanolamine (AEA). Both AEA and the phytocannabinoid, THC, have similar agonistic potency with respect to $CB_1$. THC is more potent with respect to the $CB_2$ receptor but apparently exerts its well-known psychotropic effects through the $CB_1$ receptor.

AEA is also an exogenous phytocannabinoid found in many spices and foods such as chocolate. Endogenous AEA activity is increased by palmitoylethanolamide (PEA) which apparently does not bind $CB_1$ or $CB_2$ but may be additive or synergistic when both are present, possibly through AEA synthesis induction by PEA. One metabolic pathway for AEA is enzymatic oxygenation by cytochrome P450 hydroxylates and by lipoxygenases to yield hydroperoxy- and hydroxy-derivatives of AEA. AEA also serves as a substrate for cyclooxygenase-2 resulting in the $PGE_2$ derivative of AEA. An enzyme responsible for continuous removal of AEA and related cannabinoids is fatty acid amide amidohydrolase (FAAH).

The other predominant cannabinoid in mammals, especially in the neurological system is 2-Arachidonylglycerol (2AG). Whereas AEA has a binding preference for $CB_1$ over $CB_2$, 2AG has similar agonistic affinity for each.

2AG can be metabolized rapidly to yield arachidonic acid and glycerol. Rapid elimination of 2AG from the extracellular fluid would be expectedly advantageous given that 2AG exhibits potent biological activities directed at or in diverse tissues and cells. Any misdirected excess 2AG might exert deleterious and undesirable effects. A capacity for rapid clearance of 2AG soon after generation is essential to prevent unwanted consequences.

2AG appears to be primarily metabolized at least in some tissues by a monoacylglycerol lipase, as are other monoacylglycerols. In similarity with AEA, FAAH is available to metabolize 2AG as well. 2AG can be metabolized to 2-arachidonoyl LPA through the action of a kinase(s) to recycle 2AG in the form of glycerophospholipids such as PI. COX2 and 12-lipoxygenase can oxygenate 2AG to yield oxygenated products of 2AG (prostaglandins glyceryl ester and 12(S)-hydroperoxyeicosa-5,8,10,14-tetraenoic acid glyceryl ester).

Use of topical $PGE_2$ was reported by Kapoor et al, 2008 wherein a gel (0.25 mg/g) commercially available as a sterile translucent gel preparation containing dinoprostone 0.50 mg/2 g was applied 2×/day to treat vitilago. They report "$PGE_2$ enhances basic fibroblast growth factor (bFGF) mRNA expression in a dose-dependent fashion". Results of the study hoping to restore pigmentation to patches of light skin show successful outcomes with a trend towards improved outcomes towards the cephalic portion as opposed to extremities.

Side effects of $CB_1$ activity including, but not limited to: reduced anxiety, increased stress tolerance, food craving. The drug, rimonabant, developed by Sanofi as a weight loss drug, a cannabinoid receptor blocker, was withdrawn from the European market because of possible increased depression and at least successful suicide. Though not proven, there is suggestive evidence that $CB_1$ and/or $CB_2$ activity may be an important endogenous control on bouts of depression including some associated with PTSD.

Haplosamate derivatives are the first naturally derived cannabinomimetic compound belonging to steroid family. They represent another new chemical class of cannabinoid receptor ligands. This group of steroids includes but is not limited to: haplosamate A and haplosamate B.

Haplosamate A and desulfohaplosamate have opposite effects. Haplosamate A has strong affinity for $CB_1$. Desulfohaplosamate has higher affinity for $CB_2$. The 7-monoacetylated derivative of haplosamate A exhibits affinity to both $CB_1$ and $CB_2$ cannabinoid receptors in comparison to its parent compound. However, acetylation at C-4 or dialdehyde derivative results in the loss of affinity on both $CB_1$ and $CB_2$.

While less dramatic than anabolic steroid injection, activation of $CB_1$ and $CB_2$ results in release of epinephrine, corticosteroids, and immune calming IL-10, while decreasing pro-inflammatory IL-2. Steady supplementation with one or more synthetic or phytocannabinoid has effects that can be used to substitute for chronically used corticosteroid immune suppression, but will have a more natural control and fewer side effects. Cannabinoid mediated responses include a general calming of local (e.g., dermal, iliac, bowel, gastric, mucosal, etc.) pro-inflammatory mediators including, but not limited to: myeloperoxidase, CXCL8, IL-1β, TNF, etc. Cannabis has also been shown to suppress the immune system by activating myeloid-derived suppressor cells (MDSCs). MDSCs may help dampen the hyperactive immune system.

A class of modulating biomolecules has been characterized as "endocannabinoids". The name is derived from the receptors active in this system that also being to products from the cannabis plant. Originally two cannabinoid receptors were recognized in humans/mammals because THC, a psychoactive cannabinoid substance from Cannabis was found to interact with these proteins. These were dubbed: cannabinoid receptor 1 ($CB_1$) and cannabinoid receptor 2 ($CB_2$). AEA and 2AG were recognized as predominant endocannabinoids binding these receptors. $CB_1$ immunoreactive neurons were found in close proximity to ileal Peyer's patches and were localized in some submucosal blood vessels. However, subsequent discoveries have revealed other endobiologic compounds also binding these receptors and them additional receptors which interact with AEA and 2AG and the additional recognized compounds with endocannabinoid activity.

$GPR_{55}$ and $CB_1$ receptors modulate each other's signaling properties. GPR55 forms heteromers with another 7× transmembrane spanning/GPCR which then interacts with $CB_1$. $GPR55$-$CB_1$ heterodimer acts as a modified cannabinoid receptor that cells form to modulate activities in response to exogenous cannabinoid. This plasma membrane response is independent of cannabinoid effects on internal organelles including, but not limited to: mitochondria, peroxisomes, endoplasmic reticulum, golgi, etc.

Palmitoylethanolamide (PEA) is an endocannabinoid especially capable of downregulating mast cell activation and inflammation. AEA is also an effective endogenous agonist for the central cannabinoid receptor $CB_1$ on mast cells. PEA activity may be through $CB_2$ and other cannabinoid receptors. PEA and AEA bind to $CB_2$ but AEA may be more effective when bound to $CB_1$. This provides evidence that PEA and/or its derivatives may be used to provide anti-inflammatory therapeutic strategies specifically targeted at mast cells.

The endocannabinoid system (ECS) is an important lipid based signaling and immunomodulator system. Lipophilic compounds, those that can readily cross plasma membranes are prime activators of these endocannabinoid pathways. Research relating to medical uses of marijuana and traditional medicines has shown that at least compounds that bind $CB_1$ and $CB_2$ participate in modulating many physiological responses including, but not limited to: appetite, respiration, metabolism, inflammation, allergy, pain, neurotransmission, etc. The ECS is comprised of G-protein coupled receptors (GPCRs) including, but not limited to: $CB_1$, $CB_2$, $TRPV_1$, $TRPV_2$, $TRPV_3$, $TRPV_4$, $TRPA_1$, $TRPM_8$, $GPR_{55}$, $GPR_{18}$, etc.

Two notable catabolic enzymes, fatty acid amide hydrolase (FAAH) and monoglycerol lipase (MAGL), are involved in the breakdown of anandamide and 2AG, respectively. Simply put, less FAAH and MAGL means more AEA and 2AG. So inhibitors of these catabolic enzymes, for example by nutmeg extracts, slows breakdown and raises the available levels of AEA and 2AG generally boosting cannabinoid receptor signaling. FAAH and MAGL inhibition therefore can be used in reducing or managing pain, anxiety, hypertension and various inflammatory conditions.

In general, many plant species, especially those used for spices, have anti-allergy/anti-inflammatory activities. E.g., nutmeg interacts with the endocannabinoid system by inhibiting certain key enzymes that catabolize (break down) the two main endocannabinoids, anandamide and 2AG.

URB597 inhibits FAAH, the principle enzyme involved in degrading the lipid molecule AEA into its arachidonoyl and ethanolamide components. FAAH is a significant step in the pathway for creating prostaglandin ethanolamide compounds including D2 ethanolamide. Inhibiting FAAH raises natural AEA levels and leads to long-term cannabinoid receptor activation and pain relief. URB937, is another p-hydroxyphenyl-O-arylcarbamate that targets FAAH. FAAH is also responsible for the metabolism of other fatty acid amides e.g., N-oleoylethanolamine (OEA) and N-palmitoylethanolamine (PEA). FAAH inhibition maintains or increases tissue levels of anandamide in vivo.

Examples of FAAH inhibitors include but are not limited to: AM374, ARN2508, BIA 10-2474, BMS-469908, CAY-10402, JNJ-245, JNJ-1661010, JNJ-28833155, JNJ-40413269, JNJ-42119779, JNJ-42165279, LY-2183240, cannabidiol, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597 (KDS-4103), URB694, URB937, VER-156084, V-158866, AM3506, AM6701, CAY10435, CAY10499, IDFP, JJKK-048, JNJ-40355003, JNJ-5003, JW618, JW651, JZL184, JZL195, JZP-372A, KML29, MAFP, MJN110, ML30, N-arachidonoyl maleimide, OL-135, OL92, PF-04457845, SA-57, ST4070, URB880, URB937, etc.

β-caryophyllene, a phytocannabinoid, and/or its oxides act as full agonists of the $CB_2$-receptor where they exert anti-inflammatory and analgesic effects that are mediated through $CB_2$, but not $CB_1$. Another phytocannabinoid, salvinorin A, from the plant species *Salvia divinorum* extract is a terpenoid that interacts with a cannabinoid receptor, not yet characterized that apparently forms only in inflammatory conditions. This uncharacterized receptor also acts as a κ-opioid receptor. Many sages produce similar compounds with some activity, but whose activities have not been followed in detail to identify receptor interactions. Myrcene is a major constituent of the essential oil of hops and appears to be related to opioid "high" possibly by agonizing opioid receptors or possibly by antagonizing opioid degradation. Plant sources are hops, verbena and *cannabis*. Myrcene is also found in lemongrass, thyme and mango. Echinacea contains multiple N-alkylamides that have cannabinoid mimetic effects.

Cannabigerol class: cannabigerolic acid (CBGA) (antibiotic); cannabigerolic acid monomethylether (CBGAM); cannabigerol (CBG) (antibiotic, antifungal, anti-inflammatory, analgesic); cannabigerol monomethylether (CBGM); cannabigerovarinic acid (CBGVA); cannabigerovarin (CBGV).

Cannabichromene class: Cannabichromenic acid (CBCA); cannabichromene (CBC) (antibiotic, antifungal, anti-inflammatory, analgesic); cannabichromevarinic acid (CBCVA); cannabichromevarin (CBCV); Cannabidiolic acid (CBDA) (antibiotic); cannabidiol (CBD) ((antioxidant, anxiolytic, antispasmodic, anti-inflammatory, analgesic); cannabidiol monomethylether (CBDM); cannabidiol $C_4$ (CBD-C4); cannabidivarinic acid (CBDVA); cannabidivarin (CBDV); cannabidiorcol (CBD-C1); $\Delta^9$-tetrahydrocannabinolic acid A (THCA-A); $\Delta^9$-tetrahydrocannabinolic acid B (THCA-B); 6a,10a-trans-6a,7,8,10a-tetrahydro-6,6,9-trimethyl-3-pentyl-6H-dibenzo[b,d]pyran-1-ol, ($\Delta^9$ tetrahydrocannabinol, THC) (analgesic, antioxidant, antiemetic, anti-inflammation); $\Delta^9$-tetrahydrocannabinolic acid-C4 (THCA-C4); $\Delta^9$-tetrahydrocannabinol-C4 (THC-C4); $\Delta^9$-tetrahydrocannabivarinic acid (THCVA); $\Delta^9$-tetrahydrocannabivarinic (THCV); $\Delta^7$-cis-isotetrahydrocannabivarin; $\Delta^9$-tetrahydrocannabiorcolic acid (THCA-C1); tetrahydrocannabiorcol (THC-C1).

$\Delta^8$-tetrahydrocannabinol class: $\Delta^8$-tetrahydrocannabinolic acid ($\Delta^8$-TCA); $\Delta^8$-tetrahydrocannabinol ($\Delta^8$-THC).

Cannabicyclol class: cannabicyclol (CBL); cannabicyclolic acid (CBLA); cannabicyclovarin (CBLV).

Cannabielsoin class: cannabiesoic acid A (CBEA-A); cannabiesoic acid B (CBEA-B); cannabielsoin (CBE).

Cannabinol and cannabinodiol class: cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND); cannabidivarin (CBDV).

Cannabitriol class: cannabitriol (CBT); 10-Ethoxy-9-hydroxy-$\Delta$-6a-tetrahydrocannabinol (10-EHDT); 8,9-dihydroxy-delta-6a-tetrahydrocannabinol (8,9-DHDT); cannabitriolvarin (CBTV); ethoxy-cannabitriolvarin (CBTVE).

Miscellaneous class: dehydrocannabifuran (DCBF); cannabifuran (CBF); cannabichromanon (CBCN); cannabicitran (CBT); 10-oxo-$\Delta$-6a-tetrahydrocannabinol (OTHC); $\Delta^9$-cis-tetrahydrocannabinol (cis-THC); 3,4,5,6-tetrahydro-7-hydroxy-α-α-2-trimethyl-9-n-propyl-2,6-methano-2H-1-benzoxocin-5-methanol (2H-iso-HHCV); cannabiripsol (CBR); Trihydroxy-$\Delta^9$-tetrahydrocannabinol (triOH-THC).

LEA, PEA and OEA will bind to one or more of the endogenous cannabinoid receptors, but they are also important because they maintain AEA activity through their inhibition of the FAAH enzyme that is responsible for degrading AEA. N-alkylamides exert selective effects on the $CB_2$, and have been shown to exert anti-inflammatory effects similar to AEA. Echinacea contains multiple N-alkylamides that have mimetic effects.

At least 20 flavonoid compounds, including, but not limited to: apigenin, quercetin, canniflavin A and canniflavin B, β-sitosterol, vitaxin, isovitexin, kaemferol, luteolin and orientin have been identified in the *cannabis* plant.

Magnolol, a biphenyl neolignan from *Magnolia officinalis*, magnolol acts as a partial agonist for $CB_2$, while honokiol is less potent but has full agonistic activity at $CB_1$ and antagonistic properties at $CB_2$. Malyngamide B binds both $CB_1$ and $CB_2$, with moderate potencies as an agonist anti-inflammatory compound. While many cannabinoids support nitric oxide (NO) production magnolol inhibits NO production with an $IC_{50}$~6.2 μM.

NO is a free radical formed from L-arginine by converting it to L-citrulline via nitric oxide synthase (NOS) enzymes. The reaction product of NO with superoxide generates potent oxidizing agent, peroxynitrite which is the main mediator of tissue and cellular injury. When NO and $O_2^-$ (nitric oxide free radical and superoxide anion free radical) react peroxynitrite, a powerful oxidant capable of eliciting major cell and tissue injury, results. Despite this and other possible deleterious outcomes, over the past four or five decades NO has been acknowledged as a molecule of extreme importance in intracellular and intercellular communication, slowing proliferation of, for example, smooth muscle cells; controlling platelet and endothelial adhesion; acting as a neurotransmitter; modulating mitochondrial membrane permeability; etc. As examples of NO activities, NO induced $PGE_2$ activity is part of the pathway through which the body senses dehydration and signals remedial actions across multiple organs and systems; responding to toxic events such as ethanol intoxication; a relation between cannabinoids and NO is part of joint cartilage maintenance; NO is one compensatory compound involved in multiple pathways to minimize deleterious effects of heart failure; mtNOS appears active in inducing apoptosis in infected cells; NO is closely controlled in a recovering cell following an ischemic event, sometimes support cell recovery while sometimes encouraging apoptosis; NO is part of the path for restoring proper protein folding through its actions on at least HSP70; NO controls mitochondrial growth, synthesis and fusion following intense exercise; NOS activity is induced following sleep deprivation releasing NO in support of REM sleep stages.

NO has a short half-life in aqueous solution undergoing reactions with superoxide as mentioned above to form peroxynitrite, auto-oxidize in water to form nitrous anhydride ($N_2O_3$), acidify to form nitrous acid and nitrite, lose the radical electron to form nitrosonium, etc. NO is particularly reactive with heme irons, e.g., to control lipid oxygenase reactions. NO is an important intercellular messenger through its activation of soluble guanyl cyclase leading to enzymatic and ion channel activations. NO reversibly inhibits many enzymes, especially heme containing or free radical activated enzymes; when involved in apoptosis, NO is involved in multiple paths including, but not limited to:

mitochondrial membrane permeability, mitochondrial fusion/fission balance, production of ROS and other oxidative compounds, activation of ASK1-JNK1 branch point, etc.; the NFκB ligand, RANKL is up regulated in response to depressed calcium levels; stress induced NO helps the cytoskeleton direct proteins and other biomolecules to the golgi and other organelles.

The relation by which cannabinoids, e.g., AEA, mediate intracellular and extracellular events through activating NO synthesis is well-conserved evolutionarily. Plants, invertebrate animals and vertebrate animals all demonstrate this relationship. The evidence generally involves assessing NO signaling changes upon exposure to a cannabinoid compound and blocking these changes with specific inhibition of a relevant NOS enzyme. The activities and enzymes may differ between organisms, but the endocannabinoid/NOS relationship and resultant NO production are conserved. The ubiquity of applications of the NO signaling systems is further evidenced by the incorporation of an NOS enzyme in the mitochondrial inner membrane where it is implicated in peroxynitrite formation and cytochrome c oxidase reaction rates.

Cannabinolic phyto-compounds or derivatives include but are not limited to: abinene, α-pinene, 4,8-dimethyl-1,7-nonadien-4-ol, 2-hydroxy-4-methyl-valeric, acid methyl ester, octanal, O-cymene, eucalyptol, α-phellandrene, cis-sabinene, hydroxide, myrcenol, terpinen-4-ol, α-terpineol, β-thujene, ç-terpinene, trans-α-ocimene, carveol, β-citral, guanidine, geraniol, bornyl, acetate, β-pinene, thymol, geranic, acid methyl ester, α-terpinyl acetate, d-limonene, eugenol, geranyl acetate, dihydrocarvyl acetate, α-ylangene, cis-dodec-5-enal, 3-phenyl-2-propenoic, acid methyl ester, β-elemene, c, vanillin, epoxy-α-terpenyl acetate, butanoic, acid 2-methyl-, 3,7-dimethyl-2,6-octadienyl ester, 1-methyl-4-(1-acetoxy-1-methylethyl)-cyclohex-2-enol, 1,2,3,4,4a,5, 6,8a-octahydro-4a,8-dimethyl-2-(1-methylethenyl)-, [2r-(2à,4aà,8aá)]-naphthalene, p-mentha-1(7),8-dien-2-ol, ç-muurolene hydroxy-α-terpenyl acetate, nerolidol, geranyl bromide, (−)-α-panasinsene, pyrocatechol, ç-elemene, 9,10-dehydro-isolongifolene, à-calacorene, cis-verbenol acetic, acid, 1-methyl-1-(4-methyl-5-oxo-cyclohex-3-enyl)ethyl ester, alloaromadendrene, z,z-2,6-dimethyl-3,5,7-octatriene-2-ol, 4-epi-cubedol, 2-oxabicyclo[2.2.2]octan-6-ol, 1,3,3-trimethyl-acetate, patchoulane, farnesol, caryophyllene oxide, cis-lanceol, ledene oxide-(ii), farnesol acetate, 6-epi-shyobunol, falcarinol, phytol, aromadendrene oxide-(2), heptacosane, longipinene, epoxide, hentriacontane, decamethyl-cyclopentasiloxane, geranyl, isobutyl, hexamethyl-cyclotrisiloxane, 1-docosene, tetratetracontane, dodecamethyl-cyclohexasiloxane, etc.

Supplementation with cannabinoid active substances can facilitate the cells' and the organisms mitochondrial rebalancing.

Marihuana inhibits dihydrotestosterone binding to the androgen receptor.

According to the study, bald men tend to have an abnormal amount of a protein called prostaglandin D2 on their scalps. This protein and its derivatives block hair growth.

The conversion of AEA to prostaglandins (PG) including, but not limited to: D2, E2, F2, G2, H2, I2, J2, etc. antagonizes the cadherin inflammation calming functions. H2 is readily converted to D2, E2, F2, I2, F1α, and thromboxanes. D2 is a major prostaglandin produced by mast cells and binds to the receptors PTGDR (DP1) and CRTH2 (DP2). This recruits Th2 cells, eosinophils, and basophils leading to an inflammatory response. D2 is a critical component in development of allergic disease responses such as asthma and therefore is of prime interest. E2/F2, I2/F1α and thromboxanes are separate production branch offshoots from H2 that can compete with D2 production.

$PGD_2$ inhibitors are a class of chemical components that exert an inhibitory effect on the synthesis, release, or effects of $PGD_2$ in vitro or in vivo. $PGD_2$ inhibition was researched in the context of treating asthma, allergic rhinitis and similar disease states. Such compounds and those for example listed and described in US Application 20150072963, US Application 20160346186 and/or US Application 20110021599, the contents of each where they relate to $PGD_2$ inhibitors herein incorporated in the entirety of their relevant disclosures by reference, advantageously formulated or reformulated for topical administration are preferred components of applications of the present invention.

Prostaglandin D2-glycerol ester was found to decrease macrophage activation, and this effect was dependent on ABDH[HD]6 activity (α/β-hydrolase domain 6; see also ABHD 12) that revert 2AG (second cannabinoid after AEA).

In gut tissue, activation of $CB_1$ receptors by cannabinoids, plant-derived, endogenous or synthetic, effectively reduces both gastric acid secretion and gastric motor activity, and decreases the formation of gastric mucosal lesions induced by stress, pylorus ligation, nonsteroidal anti-inflammatory drugs (NSAIDs) or alcohol, partly by peripheral, partly by central mechanisms. Similarly, indirect activation of cannabinoid receptors through elevation of endocannabinoid levels by globally acting or peripherally restricted inhibitors of their ligand metabolizing enzymes (FAAH, MAGL) or by inhibitors of their cellular uptake reduces the gastric mucosal lesions induced by NSAIDs in a $CB_1$ receptor-dependent fashion.

Use of cannabinolic compounds for medical treatments is growing. Already several plant-derived cannabinoids are used in the medical practice, such as $\Delta^9$-THC (dronabinol) and its synthetic analogue, nabilone, against chemotherapy-induced nausea and emesis, and as appetite stimulants (e.g. in AIDS patients). CBD combined with $\Delta^9$-THC (nabiximols) is used to relief neuropathic pain and spasticity in multiple sclerosis, and as an adjunctive analgesic treatment in advanced cancer pain.

Synthetic cannabinoid derivatives may differ from the natural ones in several aspects, e.g. in pharmacokinetic properties or in binding affinity to the different cannabinoid receptors. For example methanandamide, an amidase resistant chiral analogue of AEA possesses higher metabolic stability than its parent compound. WIN 55,212-2, an aminoalkylindole derivative is a potent agonist at both $CB_1$ and $CB_2$ receptors and one of the most frequently used synthetic cannabinoids. It produces effects similar to those of $\Delta^9$-THC, although it has an entirely different chemical structure. Differences in binding affinity to different cannabinoid receptors may result in selective agonists at $CB_1$ or $CB_2$ receptors. For example, ACEA (arachidonoyl-2'-chloroethylamide) prefers $CB_1$ receptors, while JWH 133 (3-(1', 1'-Dimethylbutyl)-1-deoxy-delta8-THC), or GP1a (1-(2',4'-dichlorophenyl)-6-methyl-N-piperidine-1-yl-1,4-dihydroindeno[1,2-c]pyrazole-3-carboxamide) are selective for $CB_2$ receptors. Moreover, differences in distribution may result either in global actions or peripherally restricted effects, such as the peripherally acting $CB_{1/2}$ agonist AZD 1940 and AZD 1704.

Activation of $CB_1$ and $CB_2$ receptors can be achieved not only through binding by the natural and synthetic cannabinoids provided, but also secondarily, by elevating of the level of existing endocannabinoids in the vicinity of cannabinoid receptors, e.g., by blocking their degradation and/ or uptake. AEA and 2AG levels are regulated in vivo by catabolic enzymes, e.g., FAAH, which hydrolyzes AEA into AA and ethanolamine, and monoacylglycerol lipase (MAGL), which is the main effector of 2AG hydrolysis. However, we must remember additional enzymes, e.g., the COX, lipooxygenases and cytochrome P450 enzymes that is a given circumstance may also have or be induced to have a significant role in degradation of the endocannabinoids. Extracellular cannabinoids are constantly removed from circulation or interstitium but uptake into the cells and metabolism.

To date over 120 cannabinoids, the so-called phytocannabinoids (pCB), have been isolated from the *cannabis* plant. Most phytocannabinoids share common structural features that include a dibenzopyran ring and a hydrophobic alkyl chain. The most abundant cannabinoids in the plant are $\Delta^9$-tetrahydrocannabinol ($\Delta^9$-THC or simply, THC), $\Delta^8$-tetrahydrocannabinol ($\Delta^8$-THC), cannabinol (CBN), cannabidiol (CBD), cannabigerol (CBG), and cannabichromene (CBC), $\Delta^9$-tetrahydrocannabivarin (THCV), cannabivarin (CBV), cannabidivarin (CBDV). Despite their lower pres- Additional endocannabinoids identified to date include N-arachidonoyl dopamine (NADA) and virodhamine. N-arachidonoyl-dopamine (NADA) is an endogenous "capsaicin-like" substance in mammalian nervous tissues. NADA activates cannabinoid $CB_1$ receptors, but not the dopamine $D_1$ and $D_2$ receptors. Virodhamine is arachidonic and ethanolamine joined by an ester linkage.

The $CB_2$ receptor in general recognizes the same structural groups of cannabinoid agonists as $CB_1$, with differing affinities in some cases, for example $CB_2$ has higher affinity for aminoalkylindoles.

The discussion of specific combinations of treatments, protocols, compounds and/or exemplary uses are for illustration of how the present invention might be applied in one or more specific circumstances. Such are not intended to exclude other potential embodiments not specifically discussed herein.

Application 62/609,384 and Ser. No. 15/954,582 are hereby incorporated by reference in their entireties. The CRF submitted herewith as a .txt document has identical sequence disclosure for the 3 applications, the content of which is incorporated by reference in its entirety and is reproduced on the following page.

SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Pro Val Asn Phe Lys Phe Leu Ser His
1               5 ence in the plant, other phytocannabinoids such as cannabinodiol (CBND), cannabielsoin (CBE), cannabicyclol (CBL) and cannabitriol (CBT) have also been the subjects of study in the last decades.

The different phytocannabinoids show different relative affinities for $CB_1$ and $CB_2$ receptors. In addition, over the last years, receptor targets outside the classic endocannabinoid system have been identified as binding sites and action centers for certain plant cannabinoids. These compounds have been shown to interact with other G-protein coupled receptors such as the putative cannabinoid receptors GPR55 or GPR18, and other well-known GPCRs such as the opioid or the serotonin receptors. In addition, several papers have reported the ability of certain phytocannabinoids to modulate nuclear receptors, ligand-gated ion channels or transient receptor potential (TRP) channels, among others.

For example, in the synthetic realm, SR141716A, the first reported CB1 antagonist displays nanomolar $CB_1$ affinity (Ki=1.98±0.13 nM), but very low affinity for $CB_2$. SR141716A has acts as a competitive antagonist and an inverse agonist in cells transfected with exogenous $CB_1$ receptor, and in cells endogenously expressing $CB_1$. Several additional $CB_1$ antagonists have been reportedly synthesized, including, but not limited to: LY-320135, 0-1184, CP-272871, URB447, a class of benzocycloheptapyrazoles, a novel series of 3,4-diarylpyrazolines and biarylpyrazolyl oxadiazoles. A first peptide $CB_1$ inverse agonist, hemopressin (HP; PVNFKFLSH) (SEQ ID No. 1), has also been reported.

The invention claimed is:

1. A therapeutic product comprising i), a nitric oxide inducing cannabinoid active compound selected from the group consisting of: $\Delta^8$-tetrahydrocannabinolic acid ($\Delta^8$-TCA), $\Delta^8$-tetrahydrocannabinol ($\Delta^8$-THC), cannabiesoic acid A (CBEA-A); cannabiesoic acid B (CBEA-B), cannabieson (CBE), cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND), cannabinidivarin (CBDV), cannabitriol (CBT); 10-Ethoxy-9-hydroxy-$\Delta$-6a-tetrahydrocannabinol (10-EHDT); 8,9-dihydroxy-delta-6a-tetrahydrocannabinol (8,9-DHDT); cannabitriolvarin (CBTV), ethoxy-cannabitriolvarin (CBTVE), dehydrocannabifuran (DCBF); cannabifuran (CBF); cannabichromanon (CBCN); cannabicitran (CBT); 10-oxo-4-6a-tetrahydrocannabinol (OTHC), $\Delta^9$-cis-tetrahydrocannabinol (cis-THC); 3,4,5,6-tetrahydro-7-hydroxy-α-α-2-trimethyl-9-n-propyl-2,6-methano-2H-1-benzoxocin-5-methanol (2H-iso-HHCV); cannabiripsol (CBR), trihydroxy-$\Delta^9$-tetrahydrocannabinol (triOH-THC), abinene, α-pinene, 4,8-dimethyl-1,7-nonadien-4-ol, 2-hydroxy-4-methyl-valeric, acid methyl ester, octanal, O-cymene, eucalyptol, α-phellandrene, cis-sabinene, hydroxide, myrcenol, terpinen-4-ol, α-terpineol, β-thujene, ç-terpinene, trans-α-ocimene, carveol, 2-arachidonoyl-glycerol, β-citral, guanidine, geraniol, bornyl, acetate, β-pinene, thymol, geranic, acid methyl ester, α-terpinyl acetate, d-limonene, eugenol, geranyl acetate, dihydrocarvyl acetate, α-ylangene, cis-dodec-5-enal, 3-phenyl-2-propenoic, acid methyl ester, β-elemene, c, vanillin, epoxy-α-terpenyl acetate, butanoic, acid 2-methyl-, 3,7-dimethyl-2,6-octadienyl ester, 1-methyl-4-(1-acetoxy-1-methylethyl)-cyclohex-2-enol, 1,2,3,4,4a,5,6,8a-octahydro-4a,8-dimethyl-2-(1-methylethenyl)-, [2r-(2à,4aà, 8aá)]-naphthalene, p-mentha-1 (7),8-dien-2-ol, ç-muurolene hydroxy-α-terpenyl acetate, nerolidol, geranyl bromide, (−)-α-panasinsen, pyrocatechol, ç-elemene, 9,10-dehydro-isolongifolene, à-calacorene, cis-verbenol acetic, acid, 1-methyl-1-(4-methyl-5-oxo-cyclohex-3-enyl)ethyl ester, alloaromadendrene, z,z-2,6-dimethyl-3,5,7-octatriene-2-ol, 4-epi-cubedol, 2-oxabicyclo [2.2.2]octan-6-ol, 1,3,3-trimethyl-acetate, patchoulane, farnesol, caryophyllene oxide, cis-lanceol, ledene oxide-(ii), farnesol acetate, 6-epi-shyobunol, falcarinol, phytol, aromadendrene oxide-(2), heptacosane, longipinene, epoxide, hentriacontane, decamethyl-cyclopentasiloxane, geranyl, isobutyr, hexamethyl-cyclotrisiloxane, 1-docosene, tetratetracontane, dodecamethyl-cyclohexasiloxane, methanandamide, LY-320135, 0-1184, CP-272871, URB447, SR141716A, WIN 55,212-2, ACEA, JWH 133, GP1a, AZD 1940 and AZD 1704; and ii) at least one separate compound of a hair growth augmenter selected from the group consisting of: a 5-α reductase inhibitor, an androgen receptor blocking compound in active or proactive form, a flavonoid compound, a $PGD_2$ activity inhibitor, a compound that decreases $PGD_2$ synthesis, and a cannabinoid receptor synthesis inducer.

2. The therapeutic product of claim 1 wherein administration to the scalp decreases the time length of the telegenic phase of a significant number of hair follicles (HF)s.

3. The therapeutic product of claim 1 wherein administration to the scalp decreases hair growth interference wrought by dihydrotestosterone.

4. The therapeutic product of claim 1 wherein administration to the scalp decreases hair growth interference wrought by prostaglandin $D_2$.

5. The therapeutic product of claim 1 wherein said nitric acid inducing cannabinoid compound agonizes a receptor selected from the group consisting of: $CB_1$, $CB_2$, $TRPV_1$, $TRPV_2$, $TRPV_3$, $TRPV_4$, $TRPA_1$, $TRPM_8$, $GPR_{55}$ and $GPR_{18}$.

6. The therapeutic product of claim 1 wherein ii) comprises at least one flavonoid.

7. The therapeutic product of claim 6 wherein said flavonoid is selected from the group consisting of: apigenin, quercetin, cannflavin A and cannflavin B, β-sitosterol, vitexin, isovitexin, kaempferol, luteolin and orientin.

8. The therapeutic product of claim 6 wherein said flavonoid is selected from the group consisting of: 3,3',4',5,7-pentahydroxyflavone, 2-(4-hydroxy-3-propoxy-phenyl)-chroman-3,5,7-triol, 2-(3-hydroxy-4-propoxy-phenyl)-chroman-3,5,7-triol; 2-(3-ethoxy-4-hydroxy-phenyl)-chroman-3,5,7-triol, 2-(4-ethoxy-3-hydroxy-phenyl)-chroman-3,5,7-triol, 2-(3,4-dihydroxy-phenyl)-3-propoxy-chroman-5,7-diol, methyl 4-((2R,3R)-3-hydroxy-5,7-dimethoxychroman-2-yl)-2-methoxybenzoate, methyl 5-((2R,3R)-3-hydroxy-5,7-dimethoxychroman-2-yl)-2-methoxybenzoate, (4-((2R,3R)-3-hydroxy-5,7-dimethoxychroman-2-yl)-2-methoxyphenyl) (4-methylpiperazin-1-yl)methanone, ethyl 2-(4-((2R,3R)-3-hydroxy-5,7-dimethoxychroman-2-yl)-2-methoxyphenoxy)acetate, ethyl 2-(5-((2R,3R)-3-hydroxy-5,7-dimethoxychroman-2-yl)-2-methoxyphenoxy)acetate, 2-(4-((2R,3R)-3-hydroxy-5,7-dimethoxychroman-2-yl)-2-methoxyphenoxy) acetic acid, ethyl 2-(2-hydroxy-4-((2R,3R)-3,5,7-trihydroxychroman-2-yl) phenoxy)acetate, ethyl 2-(2-hydroxy-5-((2R,3R)-3,5,7-trihydroxychroman-2-yl) phenoxy)acetate, (2R,3R)-2-(3,4-dihydroxyphenyl)-3-me-thoxychroman-5,7-diol, ((2R,3R)-2-(3,4-dihydroxyphenyl)-3-ethoxychroman-5,7-diol, (2R,3R)-2-(3,4-dihydroxyphenyl)-5,7-dihydroxychroman-3-yl acetate, 1-(((2R,3R)-2-(3,4-dihydroxyphenyl)-5,7-dihydroxychroman-3-yl)oxy) ethyl isobutyrate, (((2R,3R)-2-(3,4-dihydroxyphenyl)-5,7-dihydroxychroman-3-yl)oxy) methyl diisopropylcarbamate, tert-butyl (((((2R,3R)-2-(3,4-dihydroxyphenyl)-5,7-dihydroxychroman-3-yl)oxy) methyl) carbonate, 4-((2R,3R)-3,5,7-trihydroxychroman-2-yl)-1,2-phenylene dioctanoate, (2R,3R)-2-(3,4-dihydroxyphenyl)-5,7-dihydroxychroman-3-yl octanoate, (2R,3R)-2-(3,4-diacetoxyphenyl) chroman-3,5,7-triyl triacetate, 4-((2R,3R) 3,5,7-trihydroxychroman-2-yl)-1,2-phenylene diacetate, 4-((2R,3R)-3,5,7-trihydroxychroman-2-yl)-1,2-phenylene diacetate and (2R,3R)-2-(3,4-dihydroxyphenyl)-3-methylchroman-3,5,7-triol.

9. The therapeutic product of claim 1 wherein said nitric acid inducing cannabinoid compound is selected from the group consisting of: cannabichromenic acid (CBCA); cannabichromene (CBC); cannabichromevarinic acid (CBCVA); cannabichromevarin (CBCV); cannabidiolic acid (CBDA); cannabidiol (CBD); cannabidiol monomethylether (CBDM); cannabidiol $C_4$ (CBD-C4); cannabidivarinic acid (CBDVA); cannabidivarin (CBDV); cannabidiorcol (CBD-C1); $Δ^9$-tetrahydrocannabinolic acid A (THCA-A); $Δ^9$-tetrahydrocannabinolic acid B (THCA-B); 6a,10a-trans-6a,7,8,10a-tetrahydro-6,6,9-trimethyl-3-pentyl-6H-dibenzo [b,d] pyran-1-ol, $Δ^9$-tetrahydrocannabinol (THC); $Δ^9$-tetrahydrocannabinolic acid-C4 (THCA-C4); $Δ^9$-tetrahydrocannabinol-C4 (THC-C4); $Δ^9$-tetrahydrocannabivarinic acid (THCVA); $Δ^9$-tetrahydrocannabivarinic (THCV); $Δ^7$-cis-isotetrahydrocannabivarin; $Δ^9$-tetrahydrocannabiorcolic acid (THCA-C1) and tetrahydrocannabiorcol (THC-C1).

10. The therapeutic product of claim 1 wherein said nitric acid inducing cannabinoid compound is selected from the group consisting of: cannabicyclol (CBL); cannabicyclolic acid (CBLA) and cannabicyclovarin (CBLV).

11. The therapeutic product of claim 1 wherein said nitric acid inducing cannabinoid compound is a $CB_1$ agonist.

12. The therapeutic product of claim 1 wherein said nitric acid inducing cannabinoid compound is a $CB_2$ agonist.

13. The therapeutic product of claim 1 wherein said nitric acid inducing cannabinoid compound comprises a $TRPV_1$ agonist.

14. The therapeutic product of claim 1 further comprising a compound selected from the group consisting of: L-arginine and L-citrulline.

15. The therapeutic product of claim 1 wherein ii) comprises a compound that reduces $PGD_2$ binding to $GPR_{44}$.

16. The therapeutic product of claim 1 wherein said nitric acid inducing cannabinoid active compound is a substance inhibiting at least one cannabinoid metabolizing enzyme.

17. The therapeutic product of claim 16 wherein said metabolizing enzyme is selected from the group consisting of: FAAH and MAGL.

18. The therapeutic product of claim 1 comprising a compound A that decreases $PGD_2$ synthesis wherein said compound A increases activity of an arachidonate depleting pathway which does not synthesize $PGD_2$.

19. The therapeutic product of claim 18 wherein said arachidonate depleting pathway is selected from the group consisting of enzymes systems or pathways resulting in the synthesis of: $PGE_2$, $PGI_2$, $PGF_2$, $PGI_2$, $PGF_1α$, $PGF_2α$ and thromboxanes.

20. The therapeutic product of claim 11 wherein ii) is selected from the group consisting of: a 5-α reductase inhibitor, a PGD$_2$ activity inhibitor, and an androgen receptor blocking compound in active or pro-active form.

21. The therapeutic product of claim 20 comprising: a COX1 inhibitor.

22. The therapeutic product of claim 21 wherein said COX1 inhibitor is selected from the group consisting of: valeryl salicylate, Cox-1 Inhibitor II, FR122047 hydrate, resveratrol and SC 560.

23. The therapeutic product of claim 20 comprising a PGD$_2$ activity inhibitor.

24. The therapeutic product of claim 22 wherein said COX1 inhibitor is resveratrol.

25. The therapeutic product of claim 23 wherein said PGD$_2$ activity inhibitor is luteolin.

26. The therapeutic product of claim 1 in a delivery format selected from the group consisting of: topical gel, mist, cream, low viscosity liquid, ointment spray, dermal patch, shampoo and conditioner.

27. A method comprising delivering a therapeutic product-comprising i), a nitric oxide inducing cannabinoid active compound selected from the group consisting of:

Δ$^8$-tetrahydrocannabinolic acid (Δ$^8$-TCA), Δ$^8$-tetrahydrocannabinol (Δ$^8$-THC), cannabiesoic acid A (CBEA-A); cannabiesoic acid B (CBEA-B), cannabieson (CBE), cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND), cannabinidivarin (CBDV), cannabitriol (CBT); 10-Ethoxy-9-hydroxy-Δ-6a-tetrahydrocannabinol (10-EHDT); 8,9-dihydroxy-delta-6a-tetrahydrocannabinol (8,9-DHDT); cannabitriolvarin (CBTV), ethoxy-cannabitriolvarin (CBTVE), dehydrocannabifuran (DCBF); cannabifuran (CBF); cannabichromanon (CBCN); cannabicitran (CBT); 10-oxo-4-6a-tetrahydrocannabinol (OTHC); Δ$^9$-cis-tetrahydrocannabinol (cis-THC); 3,4,5,6-tetrahydro-7-hydroxy-α-α-2-trimethyl-9-n-propyl-2,6-methano-2H-1-benzoxocin-5-methanol (2H-iso-HHCV); cannabiripsol (CBR), trihydroxy-Δ$^9$-tetrahydrocannabinol (triOH-THC), abinene, α-pinene, 4,8-dimethyl-1,7-nonadien-4-ol, 2-hydroxy-4-methyl-valeric, acid methyl ester, octanal, O-cymene, eucalyptol, α-phellandrene, cis-sabinene, hydroxide, myrcenol, terpinen-4-ol, α-terpineol, β-thujene, ç-terpinene, trans-α-ocimene, carveol, 2-arachidonoyl-glycerol, β-citral, guanidine, geraniol, bornyl, acetate, β-pinene, thymol, geranic, acid methyl ester, α-terpinyl acetate, d-limonene, eugenol, geranyl acetate, dihydrocarvyl acetate, α-ylangene, cis-dodec-5-enal, 3-phenyl-2-propenoic, acid methyl ester, β-elemene, c, vanillin, epoxy-α-terpenyl acetate, butanoic, acid 2-methyl-, 3,7-dimethyl-2,6-octadienyl ester, 1-methyl-4-(1-acetoxy-1-methylethyl)-cyclohex-2-enol, 1,2,3,4,4a,5,6,8a-octahydro-4a,8-dimethyl-2-(1-methylethenyl)-, [2r-(2à,4aà,8aá)]-naphthalene, p-mentha-1 (7),8-dien-2-ol, ç-muurolene hydroxy-α-terpenyl acetate, nerolidol, geranyl bromide, (–)-α-panasinsen, pyrocatechol, ç-elemene, 9,10-dehydro-isolongifolene, à-calacorene, cis-verbenol acetic, acid, 1-methyl-1-(4-methyl-5-oxo-cyclohex-3-enyl)ethyl ester, alloaromadendrene, z,z-2,6-dimethyl-3,5,7-octatriene-2-ol, 4-epi-cubedol, 2-oxabicyclo [2.2.2]octan-6-ol, 1,3,3-trimethyl-acetate, patchoulane, farnesol, caryophyllene oxide, cis-lanceol, ledene oxide-(ii), farnesol acetate, 6-epi-shyobunol, falcarinol, phytol, aromadendrene oxide-(2), heptacosane, longipinene, epoxide, hentriacontane, decamethyl-cyclopentasiloxane, geranyl, isobutyr, hexamethyl-cyclotrisiloxane, 1-docosene, tetratetracontane, dodecamethyl-cyclohex-asiloxane, methanandamide, LY-320135, 0-1184, CP-272871, URB447, SR141716A, WIN 55,212-2, ACEA, JWH 133, GP1a, AZD 1940 and AZD 1704; and ii) at least one separate compound a hair growth augmenter selected from the group consisting of: a 5-a reductase inhibitor, an androgen receptor blocking compound in active or pro-active form, a flavonoid compound, a PGD$_2$ activity inhibitor, a compound that decreases PGD$_2$ synthesis, and a cannabinoid receptor synthesis inducer to a human scalp whose hair retention is desired, said method further comprising: locating a telogenic or anagenic follicle on said human scalp; delivering said therapeutic product to said located follicle.

* * * * *